US011918979B2

(12) United States Patent
Gotzmann et al.

(10) Patent No.: US 11,918,979 B2
(45) Date of Patent: Mar. 5, 2024

(54) METHOD FOR ACTIVATING A PHOTOCATALYTICALLY ACTIVE OUTER LAYER DEPOSITED ON A COMPOSITE

(71) Applicant: Fraunhofer-Gesellschaft zur Förderung der angewandten Forschung e.V., Munich (DE)

(72) Inventors: Gaby Gotzmann, Dresden (DE); Uwe Vogel, Dresden (DE); Daniel Glöss, Dresden (DE); Jessy Schönfelder, Dresden (DE); Philipp Wartenberg, Dresden (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 627 days.

(21) Appl. No.: 17/263,611

(22) PCT Filed: Jul. 25, 2019

(86) PCT No.: PCT/EP2019/070058
§ 371 (c)(1),
(2) Date: Jan. 27, 2021

(87) PCT Pub. No.: WO2020/021018
PCT Pub. Date: Jan. 30, 2020

(65) Prior Publication Data
US 2021/0291149 A1 Sep. 23, 2021

(30) Foreign Application Priority Data
Jul. 27, 2018 (DE) .................... 10 2018 118 227.9

(51) Int. Cl.
*A61L 2/00* (2006.01)
*A61L 2/08* (2006.01)
(Continued)

(52) U.S. Cl.
CPC ............. *B01J 21/063* (2013.01); *A61L 9/205* (2013.01); *B01J 27/24* (2013.01); *B01J 35/004* (2013.01);
(Continued)

(58) Field of Classification Search
CPC .. A61L 2202/11; A61L 2202/14; A61L 2/088; A61L 2/0088
See application file for complete search history.

(56) References Cited

U.S. PATENT DOCUMENTS

| 2006/0275188 A1 | 12/2006 | Wei |
| 2015/0250907 A1 | 9/2015 | Bilenko et al. |
| 2017/0129396 A1 | 5/2017 | Salter et al. |

FOREIGN PATENT DOCUMENTS

| DE | 10 2016 120 283 A1 | 10/2016 |
| EP | 3 020 479 A1 | 5/2016 |
| JP | 2007331546 A | 12/2007 |

OTHER PUBLICATIONS

International Search Report, issued in International application PCT/EP2019/070058, dated Oct. 11, 2019, pp. 1-5, European Patent Office, Rijswijk, Netherlands.

*Primary Examiner* — Sean E Conley
(74) *Attorney, Agent, or Firm* — Crowell & Moring LLP

(57) ABSTRACT

The invention relates to a method for activating a photocatalytically active, for example titanium-dioxide-containing, outer layer (13; 23) deposited on a composite, by means of at least one element (14; 24) generating a radiation, for example for generating ultraviolet radiation. The following method steps are comprised here: •a) forming the at least one radiation-generating first element (14; 24) within the composite; •b) forming at least one sensor (16; 26) within the composite; •c) recording an actual value of a physical variable characterizing luminous radiation by means of the at least one sensor (16; 26), wherein the luminous radiation
(Continued)

is emitted by a light-generating second element (15; 25); •d) comparing the recorded actual value with a first threshold value within an evaluation device and switching on the at least one radiation-generating first element (14; 24) if the actual value is below or above the first threshold value.

11 Claims, 2 Drawing Sheets

(51) Int. Cl.
*A61L 9/20* (2006.01)
*B01J 21/06* (2006.01)
*B01J 27/24* (2006.01)
*B01J 35/00* (2006.01)
*B01J 37/02* (2006.01)

(52) U.S. Cl.
CPC ......... *B01J 37/0215* (2013.01); *A61L 2/0088* (2013.01); *A61L 2/088* (2013.01); *A61L 2202/11* (2013.01); *A61L 2202/14* (2013.01); *A61L 2209/111* (2013.01)

METHOD FOR ACTIVATING A PHOTOCATALYTICALLY ACTIVE OUTER LAYER DEPOSITED ON A COMPOSITE

CROSS-REFERENCE TO RELATED APPLICATIONS

This application is a 371 nationalization of international patent application PCT/EP2019/070058 filed Jul. 25, 2019, which claims priority under 35 USC § 119 to German Patent Application DE 102018118227.9, filed Jul. 27, 2018. The entire contents of each of the above-identified applications are hereby incorporated by reference.

DETAILED DESCRIPTION

Figure 1:
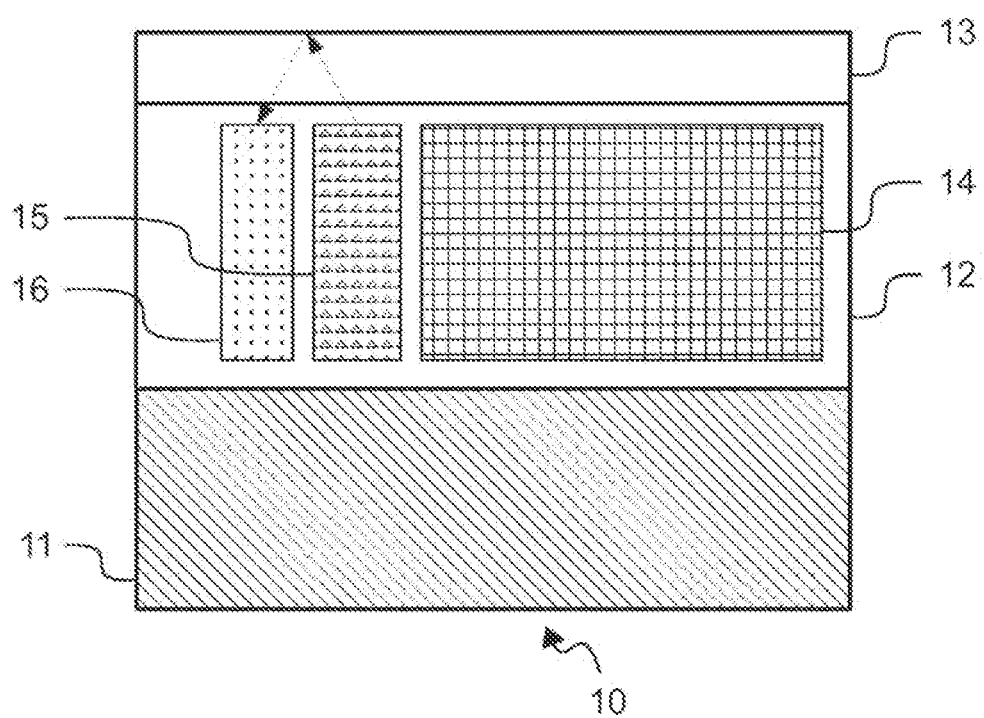
FIG. 1 illustrates a component suited to embody the method according to the invention in a schematic cross-sectional representation.

The invention relates to a method for activating a photocatalytically active outer layer deposited on a composite using radiation, wherein a composite as defined by the invention comprises a substrate and a system of layers consisting of one or several layers deposited on the substrate.

The use of utility objects necessarily has the effect that organic contaminants and biofilms are deposited on the surface of the utility objects. Said organic contaminants and biofilms involve the risk of pathogen transmission. One possible form of mitigating the risk is to design surfaces such that the ability of contaminants to adhere to the surface is minimized, as is for example known from the so-called Lotus effect.

Solutions are also known wherein the surface is equipped with anti-bacterial active ingredients in order to neutralize organic contaminants and biofilms. DE 10 2007 021 104 A1 for example proposes assigning to a substrate carrier an anti-microbial active ingredient present in colloidal and/or nanoscale form. This method has the disadvantageous effect that this approach can predominantly be used on surfaces consisting of fibers.

Another form of equipping surfaces is to use photocatalytically active materials. This frequently involves the use of titanium dioxide. DE 102 10 465 A1 for example proposes depositing a photocatalytically active thin layer on an open-pored substrate, wherein titanium dioxide is also named as the photocatalytically active material. When irradiated with light in the near-UV wavelength, the chemical structure of the material triggers photocatalysis. This neutralizes and oxidatively breaks down organic contaminants into carbon dioxide and water.

Such UV activation frequently occurs due to sun irradiation and is therefore dependent on time of day and also weather. When artificial light sources are used for UV radiation, for example in indoor environments, persons in the immediate surroundings must be reliably protected against the elevated, harmful UV content. This either results in a small distance of the light source to the irradiated surface in order to apply radiation with the lowest-possible intensity or requires UV treatment in a secured environment, e.g., the presence of persons is not permitted during the treatment. Both approaches represent an enormous restriction for the practical utility of the photocatalysis method, in particular also because activating the photocatalysis effect frequently requires hours and even up to several days.

The invention is therefore based on the technical task to create a method for activating a photocatalytically active outer layer on a composite, by means of which the disadvantages from the prior art can be overcome. In particular, the method according to the invention is intended to activate a photocatalytically active outer layer deposited on a composite independently of sunlight. The method according to the invention is further intended to determine when a photocatalytically active outer layer is to be activated.

Whereas the prior art for purposes of activating a photocatalytically active outer layer deposited on a composite only knows solutions wherein radiation activates the photocatalytically active outer layer by impacting the outer layer surface from the outside, the method according to the invention is characterized in that a photocatalytically active outer layer deposited on a composite is activated from the rear side of the outer layer with radiation, wherein at least one radiation-generating element is formed within the composite and below the photocatalytically active outer layer, and wherein the element emits a radiation to activate the photocatalytically active outer layer. The at least one radiation-generating element can for example emit UV radiation that penetrates the photocatalytically active outer layer from the rear side and that also activates the photocatalytically active outer layer on the outer layer surface.

Using the method according to the invention, it is also possible to determine whether the surface of the photocatalytically active outer layer is contaminated, and thus whether the photocatalytically active outer layer even needs to be activated.

In an embodiment, at least one light-generating second element and at least one sensor are for this purpose formed within the composite and below the photocatalytically active outer layer, wherein an actual value of a physical parameter characterizing a light radiation is recorded by the sensor, wherein said light radiation is radiated by a light-generating second element. The light-generating second element can either also be formed within the composite and below the photocatalytically active outer layer or alternatively be arranged outside of the composite.

Within the analysis device, the actual value recorded by the sensor is then compared to a first threshold value and the at least one radiation-generating first element is switched on when the actual value exceeds or drops below the first threshold value. Whether dropping below or exceeding the first threshold value results in switching on the at least one radiation-generating first element depends on what parameter of the light-generating second element is recorded by the sensor. For example, if the sensor records the intensity of the light radiation of the light-generating second element, which would be reduced by contamination on the surface of the photocatalytically active outer layer, dropping below the first threshold value would result in switching on the at least one radiation-generating first element.

In an embodiment of the invention, the radiation-generating first element is switched back off when an actual value recorded by the at least one sensor (16; 26) exceeds a second threshold value whenever dropping below the first target value results in switching on the at least one radiation-generating first element and/or the one radiation-generating first element is switched back off when an actual value recorded by the at least one sensor drops below a second threshold value whenever exceeding the first target value results in switching on the at least one radiation-generating first element.

The present invention is explained in detail as follows based on exemplary embodiments.

FIG. 1 shows a schematic representation of a component 10 based on which the method according to the invention can be embodied. Component 10 comprises a substrate 11 and a layer system 12 deposited thereon, consisting of a plurality of individual layers. The substrate 11 and the layer system 12 are for purposes of the invention referred to as a composite. A photocatalytically active layer 13 was also deposited above the layer system 12.

According to the invention, at least one first element 14 is formed below the photocatalytically active layer 13 and within the layer system 12, generating a radiation by which the photocatalytically active layer 13 can be activated. The first element 14 can for example generate UV radiation to activate the photocatalytically active layer 13. Alternatively, the first element 14 can also generate another radiation known from the prior art by which a photocatalytically active layer can be activated.

Additionally, a light-generating second element 15 is formed below the photocatalytically active layer 13 and within the layer system 12, wherein can for example generate light radiation in a wavelength range visible to the human eye. But alternatively, the light-generating second element 15 can also generate a radiation in another wavelength range, such as in the infrared or ultraviolet range.

The light radiation of the light-generating second element can be used to determine whether the surface of the photocatalytically active outer layer 13 is contaminated. The light radiation generated by the second element, which is schematically represented in FIG. 1 by an arrow originating from the second element 15, is at least partially reflected by the surface of the photocatalytically active layer 13 (dotted arrow in FIG. 1). The light radiation of the second element 15 reflected by the surface of the photocatalytically active layer 13 is recorded by a sensor 16, wherein the sensor 16 is also formed below the photocatalytically outer layer 13 and within the layer system 12. The more the surface of the catalytically active layer 13 is contaminated, the more the light radiation emitted by the second element 15 is absorbed by the contamination on the surface of the photocatalytically active outer layer 13 and/or is optically diffracted and the less reflected light radiation is recorded by the sensor 16. The actual values for the reflected light radiation recorded by the sensor 16 are forwarded to an analysis device and are compared to a target value for the intensity of the reflected light radiation. The analysis device can for example be formed within the component 10 or can alternatively also be located outside of the component 10. When an actual value drops below the target value, which means the same as that the contamination on the surface of the photocatalytically active outer layer 13 has exceeded an undesirable level of contamination, the analysis device generates a first signal by which the radiation-generating first element 14 is switched on. This activates the photocatalytically active outer layer 13, resulting in a reduction and/or deactivation of the contamination on the surface of the photocatalytically active outer layer 13.

As the contamination on the surface on the photocatalytically active outer layer 13 is reduced, the actual values recorded by the sensor 16 for the intensity of the reflected light radiation begin to climb again. When an actual value for the intensity of the reflected light radiation recorded by the sensor 16 exceeds a second target value for the intensity of the reflected light radiation, which means the same as that the surface of the photocatalytically active outer layer 13 has again reached a desirable level of cleanliness, the analysis device generates a second signal by which the radiation-generating first element 14 is switched off.

By means of the procedure of according to the invention, a photocatalytically active outer layer is only activated when this is required by the degree of contamination of the photocatalytically active outer layer. The method according to the invention is therefore particularly energy-efficient. An embodiment according to FIG. 1 also has the advantage that an external radiation source for activating the photocatalytically outer layer is not required, resulting in independence from daylight by which photocatalytically active outer layers are frequently activated.

For example, so-called bi-directional displays are known from WO 2012/163312 A1. These bi-directional displays comprise a composite consisting of a substrate and a layer system deposited thereon, wherein a plurality of light-emitting elements and a plurality of light-detecting elements are formed within the composite. Both the light-emitting elements and also the light-detecting elements are in this case each arranged nested in a matrix shape such that the light-emitting elements and the light-detecting elements are arranged next to each other in alternating positions.

Such a bi-directional display is suited for implementing the approach according to the invention described in FIG. 1. The light-emitting elements and the light-detecting elements of a bi-directional display can in this case for example be split into segments, and within each segment at least one light-emitting element of the bi-directional display can be formed as a radiation-generating first element 14, at least one light-emitting element of the bi-directional can be formed as a light-generating second element 15, and at least one light-detecting element of the bi-directional display can formed as sensor 16. Additionally, a photocatalytically active outer layer is deposited on the bi-directional display. By means of such a bi-directional display implemented according to the invention, a fingerprint sensor or a touch display can be formed that can autonomously detect surface contamination and autonomously remove and/or deactivate surface contamination independently of external radiation sources.

In an alternative embodiment of the invention, the very same component formed below the photocatalytically active outer layer 13 and within the composite can be used both as a radiation-generating first element 14 and also as a light-generating second element 15, wherein this component is for example used to generate a low-power radiation in the time intervals during which this component is used as a light-generating second element in relation to the time intervals during which the component is used as a radiation-generating first element.

Figure 2:
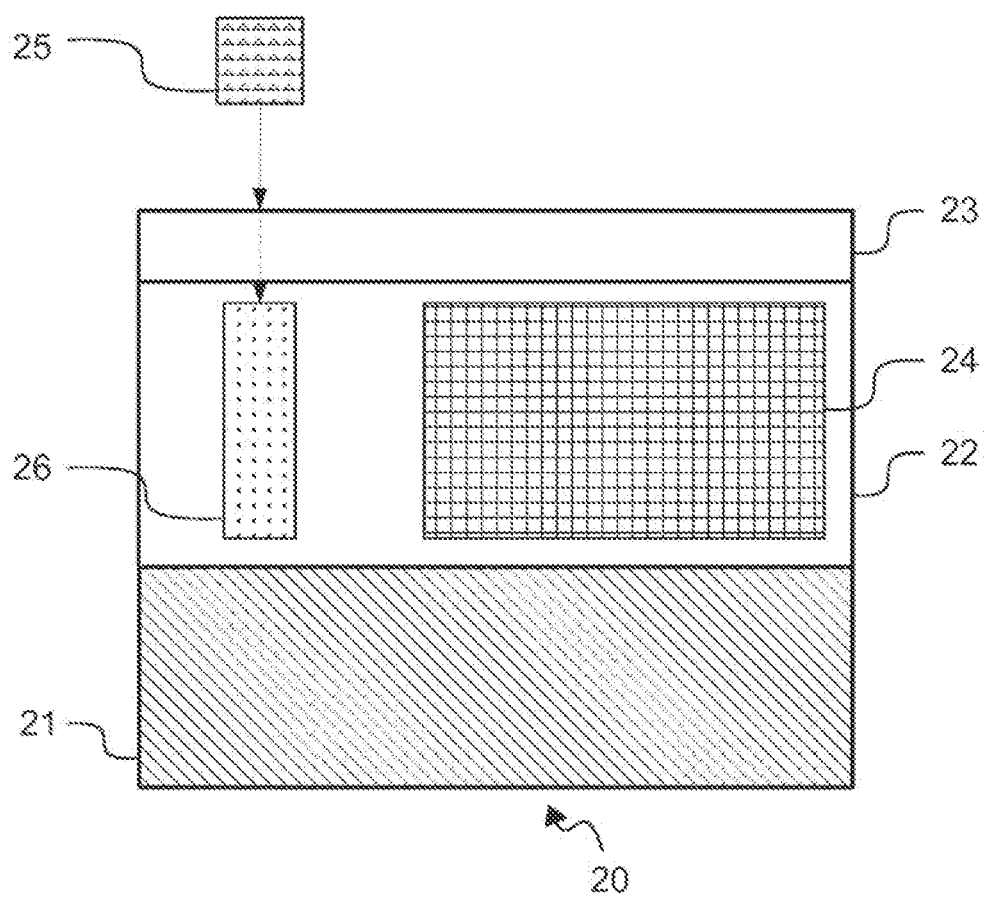
FIG. 2 illustrates an alternative component suited to embody the method according to the invention in a schematic cross-sectional representation.

A further alternative approach according to the invention is possible with a component 20 shown schematically as a cross-section in FIG. 2. Component 20 comprises a substrate 21 and a layer system 22 deposited thereon, comprising a plurality of individual layers. The substrate 21 and the layer systems 22 are for purposes of the invention together referred to as a composite. A photocatalytically active layer 23 was also deposited onto the composite above the layer system 22.

According to the invention, at least one first element 24 is formed below the photocatalytically active layer 23 and within the layer system 22, the element 24 generating a radiation by means of which the photocatalytically active layer 23 can be activated. The first element 24 can for example generate UV radiation to activate the photocatalytically active layer 23. But alternatively, the first element 24 and another can create known radiation from the prior art that can be activated by means of a photocatalytically active layer.

In this exemplary embodiment, at least one light-generating second element 25 is arranged outside of component 20, having the ability to for example generate light radiation in a wavelength range visible to the human eye. The light-generating second element 25 is in this case arranged such that it can be used to irradiate the photocatalytically active layer 23.

By means of the light radiation of the light-generating second element 25, it can be determined whether the surface of the photocatalytically active layer 23 is contaminated. The light radiation generated by the second element 25, which is schematically shown in FIG. 2 with an arrow originating from the second element 25, at least partially penetrates the photocatalytically active layer 23 (arrow with dotted line in FIG. 1) and is detected by a sensor 26 formed below the photocatalytically active layer 23 and within the layer system 22. The more the surface of the catalytically active layer 23 is contaminated, the more the light radiation emitted by the second element 25 is absorbed by the contamination on the surface of the photocatalytically active outer layer 23 and/or is optically diffracted and the less reflected light radiation is recorded by the sensor 26. The actual values for the reflected light radiation recorded by the sensor 26 are forwarded to an analysis device and are compared to a target value for the intensity of the reflected light radiation. The analysis device can for example be formed within the component 20 or can alternatively also be located outside of the component 20. When an actual value drops below the target value, which means the same as that the contamination on the surface of the photocatalytically active outer layer 23 has exceeded an undesirable level of contamination, the analysis device generates a first signal by which the radiation-generating first element 24 is switched on. This activates the photocatalytically active outer layer 23, resulting in a reduction and/or deactivation of the contamination on the surface of the photocatalytically active outer layer 23.

As the contamination on the surface on the photocatalytically active outer layer 23 is reduced, the actual values recorded by the sensor 26 for the intensity of the reflected light radiation begin to climb again. When an actual value for the intensity of the reflected light radiation recorded by the sensor 16 exceeds a second target value for the intensity of the reflected light radiation, which means the same as that the surface of the photocatalytically active outer layer 23 has again reached a desirable level of cleanliness, the analysis device generates a second signal by which the radiation-generating first element 24 is switched off.

This embodiment is likewise characterized by high energy efficiency because the photocatalytically active outer layer is only activated when required by a degree of contamination on the surface of the outer layer. But this embodiment requires an external light-generating second element 25. An artificial light source or alternatively also the sun can be used as a light-generating second element 25.

A layer that contains titanium oxide can for example be used as a photocatalytically active outer layer for the method according to the invention and also for the exemplary embodiments described above. But alternatively, any other materials known from the prior art and combinations thereof that are photocatalytically active can also be used for these layer depositions.

In an embodiment, the photocatalytically active outer layer is doped with nitrogen for the layer deposition. It has been shown that layer material doped with nitrogen absorbs radiation for activating a photocatalytically active layer particularly well, thus improving the activation of the photocatalytically active outer layer. It is therefore particularly advantageous when the photocatalytically active outer layer is formed with a nitrogen gradient such that the photocatalytically active outer layer exhibits the lowest nitrogen concentration along the boundary to the composite and the highest nitrogen concentration on the layer surface. This ensures that the photocatalytically active outer layer absorbs the radiation for activating the photocatalytically active outer layer in particular in the areas on the layer surface and therefore where a contamination of the photocatalytically active outer layer is to be removed and/or deactivated.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A method for activating a photocatalytically active outer layer deposited on a composite by means of at least one radiation-generating element, wherein the composite comprises a substrate and a layer system deposited thereon, comprising:
   Forming of at least one radiation-generating first element within the composite;
   Forming of at least one sensor within the composite;
   Recording of an actual value of a physical parameter measured by light radiation, by means of the at least one sensor, wherein the light radiation is radiated by a light-generating second element;
   Comparing of the recorded actual value to a first threshold value by an analysis device and switching on the at least one radiation-generating first element when the actual value exceeds or drops below the first threshold value.

2. The method of claim 1, wherein the radiation-generating first element is switched off when
   an actual value recorded by the at least one sensor exceeds a second threshold value whenever dropping below the first threshold value results in switching on the at least one radiation-generating first element;
   or
   an actual value recorded by the at least one sensor drops below a second threshold value whenever exceeding the first threshold value results in switching on the at least one radiation-generating first element.

3. The method of claim 1, wherein the light-generating second element is formed within the composite.

4. The method of claim 1, wherein a component can be used as the radiation-generating first element and also as the light-generating second element.

5. The method of claim 1, wherein the surface of the composite is split into segments and in that at least one radiation-generating first element, at least one light-generating second element, and at least one sensor are formed within each segment.

6. The method of claim 1, wherein an actual value is recorded, by the at least one sensor, for the intensity of the light radiation of the light-generating second element reflected on the outer boundary of the photocatalytically active outer layer.

7. The method of claim 1, wherein a light source arranged outside of the composite is used as a light-generating second element.

8. The method of claim 1, wherein a radiation-generating first element is formed as a UV radiation source.

9. The method of claim 1, wherein the photocatalytically active outer layer is formed as a titanium-oxide-based layer.

10. The method of claim 1, wherein the photocatalytically active outer layer is doped with nitrogen.

11. The method of claim 9, wherein the nitrogen concentration of the photocatalytically active outer layer is formed with a gradient such that the nitrogen concentration is lowest on the side facing the composite, and highest on the surface of the outer layer.

\* \* \* \* \*